US00PP26297P3

(12) United States Plant Patent
Meilland

(10) Patent No.: US PP26,297 P3
(45) Date of Patent: Jan. 12, 2016

(54) FLORIBUNDA ROSE PLANT NAMED 'MEIAJBETH'

(50) Latin Name: *Rosa hybrida*
Varietal Denomination: Meiajbeth

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 174 days.

(21) Appl. No.: 13/998,743

(22) Filed: Dec. 3, 2013

(65) Prior Publication Data

US 2015/0156932 P1 Jun. 4, 2015

(51) Int. Cl.
*A01H 5/02* (2006.01)

(52) U.S. Cl.
USPC ..... Plt./143

(58) Field of Classification Search
USPC ..... Plt./101, 141, 143
See application file for complete search history.

*Primary Examiner* — Susan McCormick Ewoldt
(74) *Attorney, Agent, or Firm* — Buchanan, Ingersoll & Rooney PC

(57) ABSTRACT

A new and distinct Floribunda rose plant is provided that commonly commences blooming medium in the season and forms abundantly and substantially continuously attractive near white suffused with red single blossoms. The growth habit is bushy, and strong vegetation is formed. The vegetation is dark green and bears a glossy aspect on the upper surface. The tolerance to disease is good, particularly with respect to Marsonia. The plant is particularly well suited for providing attractive ornamentation in parks and gardens.

1 Drawing Sheet

Figures 1, 2, 3, 4, 5, 6, 7, 8, 9, 10, 11, 12, 13, 14, 15:
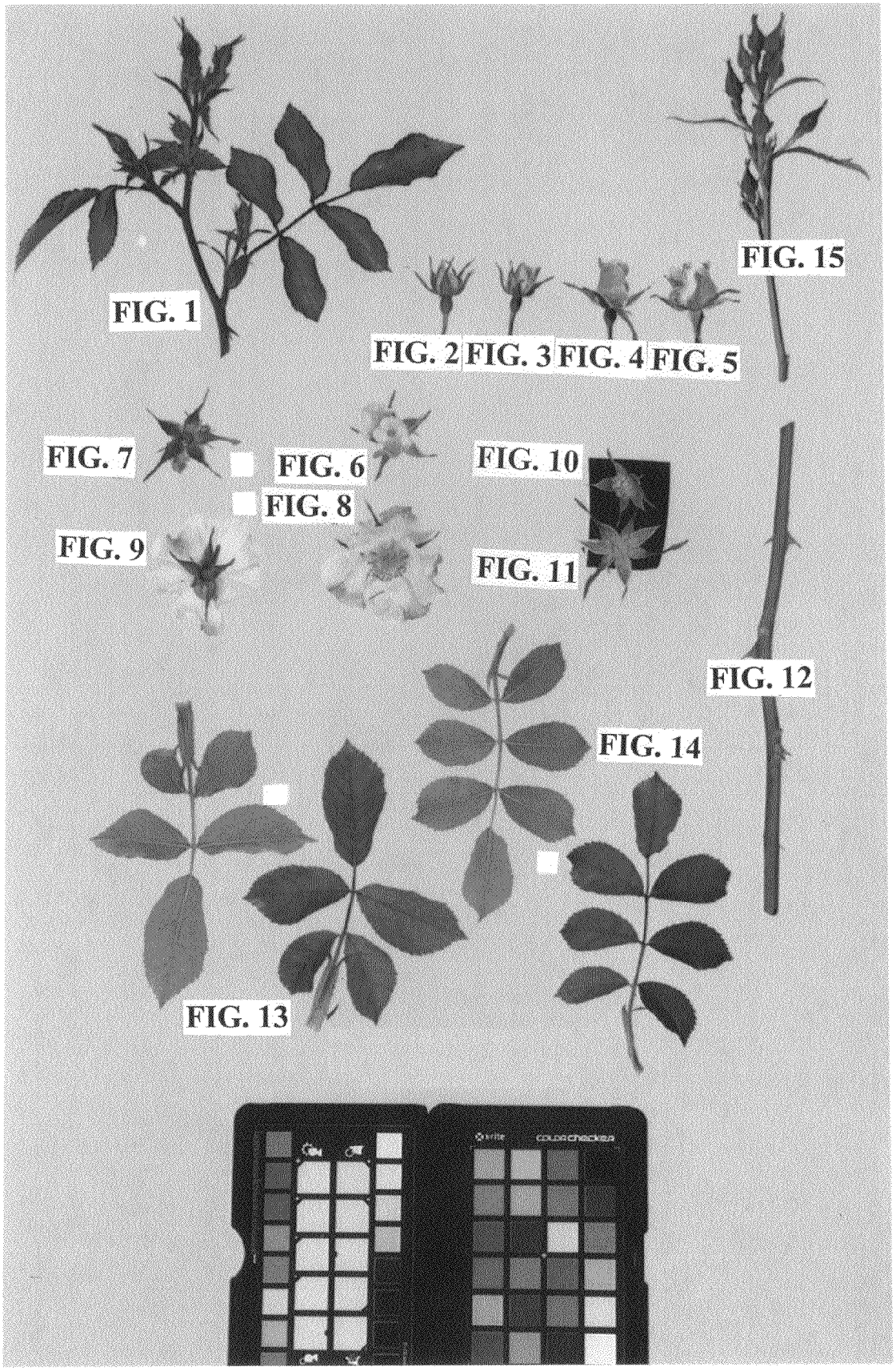

Botanical/commercial classification: *Rosa hybrida*/Floribunda Rose Plant.

Varietal denomination: cv. Meiajbeth.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was 'The Fairy' variety (non-patented in the United States). The male parent (i.e., the pollen parent) was the product of the cross of the 'Kormax' variety (non-patented in the United States) and an unnamed and unreleased seedling (non-patented in the United States).

The parentage of the new variety can be summarized as follows:

'The Fairy'×('Kormax'×unnamed seedling).

The seeds resulting from the above pollination were sown and small plants were obtained which were physically and biologically different from each other. Selective study resulted in the identification of a single plant of the new variety.

It was found that the new Floribunda rose plant of the present invention:

(a) displays a bushy growth habit with strong vegetation,
(b) forms in abundance on a substantially continuous basis attractive near white suffused with red single blossoms,
(c) exhibits dense dark green foliage with a glossy aspect on the upper surface,
(d) displays good disease tolerance particularly with respect to Marsonia, and
(e) is particularly well suited for providing attractive ornamentation in parks and gardens.

The blooming tends to commence medium in the season, during observations to date.

The new variety well meets the needs of the horticultural industry and can be grown to advantage where attractive ornamentation is to be provided.

The new variety can be readily distinguished from its ancestors. For instance, 'The Fairy' parental variety forms dissimilar light pink blossoms. The 'Kormax' variety forms dissimilar red blossoms commonly having six petals.

The new variety also can be readily distinguished from the 'Meisilimon' variety (non-patented) and the 'Meipotal' variety (U.S. Plant Pat. No. 8,841, granted Jul. 19, 1994). More specifically, the 'Meisilimon' variety forms pearl white blossoms, and 'Meipotal' variety displays a taller growth habit and forms pink blossoms with a white eye.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meiajbeth'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately three years of age and were observed during June while budded on *Rosa laxa* understock and growing outdoors at Le Cannet des Maures, Var, France. Comparative standard color information is included at the bottom.

FIG. 1—illustrates a specimen of a young shoot with unopened floral buds;

FIG. 2—illustrates a specimen of a floral bud at the opening of the sepals;

FIG. 3—illustrates a specimen of a floral bud wherein the petals are beginning to open;

FIG. 4—illustrates a specimen of a floral bud wherein the petals are more fully open;

FIG. 5—illustrates a specimen of a flower in the course of opening;

FIG. 6—illustrates a specimen of an open flower—plan view—obverse;

FIG. 7—illustrates a specimen of an open flower—plan view —reverse;

FIG. 8—illustrates a specimen of a fully open flower—plan view—obverse;

FIG. 9—illustrates a specimen of a fully open flower—plan view—reverse;

FIG. 10 —illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates specimens of leaves with five leaflets—plan view—upper surface (right) and—under surface (left);

FIG. 14—illustrates specimens of leaves with seven leaflets—plan view—upper surface (lower right) and—under surface (upper left); and FIG. 15—illustrates a cluster of buds.

DETAILED BOTANICAL DESCRIPTION

The chart used in the identification of the colors is that of The Royal Horticultural Society (R.H.S. Colour Chart-1995). The description is based on the observation of three-year-old plants during May which were budded on *Rosa laxa* understock and growing outdoors at Le Cannet des Maures, Var, France.

Class: Floribunda.

Plant:

*Growth habit*.—Bushy.

*Height*.—Commonly approximately 60 cm on average.

*Width*.—Commonly approximately 60 cm on average.

Branches:

*Color*.—Young stems: near Yellow-Green Group 146C. Adult wood: near Yellow-Green Group 146B.

*Thorns*.—On young stems: Configuration: with an obovate base. Quantity: approximately 5 on average on a stem length of 10 cm. Length: approximately 6 mm on average. Color: near Greyed-Orange Group 163C. On adult stems: Configuration: slightly curved downwards on the upper surface and concave on the under surface. Quantity: approximately 1 on average on a stem length of 10 cm. Length: approximately 1.2 cm on average. Color: near Greyed-Orange Group 166A.

Leaves:

*Stipules*.—Adnate, pectinate, narrow, approximately 1.7 cm in length on average, approximately 4 mm in width on average, near Green Group 137B on the upper surface, and near Yellow-Green Group 146C on the under surface.

*Petioles*.—Upper surface: near Green Group 137B in coloration. Under surface: near Yellow-Green Group 146C in coloration. Texture: non-glandular on the upper surface, and with a few small prickles on the under surface.

*Rachis*.—Upper surface: near Yellow-Green Group 145C in coloration. Under surface: near Yellow-Green Group 145B in coloration.

*Length*.—Approximately 12.3 cm on average for a five-leaflet leaf.

*Width*.—Approximately 9 cm on average for a five-leaflet leaf.

*Leaflets*.—Number: 3, 5 (most often), and 7. Shape: generally elliptical with an acuminate tip and an obtuse base. Size: the terminal leaflets commonly are approximately 4.6 cm in length on average and approximately 2.7 cm in width on average. Serration: slightly denticulate, small and single. Texture: physically firm and leathery. Color (young foliage): Upper surface: near Yellow-Green Group 146A. Under surface: near Yellow-Green Group 147C. Color (adult foliage): Upper surface: near Green Group 137B. Under surface: near Yellow-Green Group 146C. Venation: alternate pinnate, and commonly near Greyed-Red Group 160C in coloration.

Inflorescence:

*Number of flowers*.—Commonly approximately 3 to 15 blossoms per stem.

*Peduncle*.—Non-glandular, approximately 2 cm in length on average, approximately 1 mm in diameter on average, and near Yellow-Green Group 147C in coloration.

*Sepals*.—Upper surface: tomentose and near Yellow-Green Group 148B and 148C in coloration. Under surface: smooth and near Yellow-Green Group 147C in coloration. Shape: longish and narrow, and upright at the base. Size: approximately 1 to 1.2 cm in length on average, and approximately 3 mm in width at the widest point on average.

*Buds*.—Shape: substantially conical. Size: small. Length: approximately 5 mm on average. Width: approximately 3 mm on average at the widest point. Color as calyx breaks: Upper surface: near Red Group 36D slightly suffused with near Red Group 36C, and with a large spot of near Yellow Group 2B and 2C at the base. Under surface: near Yellow-White Group 158D slightly suffused with near Red Group 36D, with a large spot of near Yellow Group 2B and 2C at the base.

*Flower*.—Shape: cup-shaped. Diameter: approximately 4 to 5 cm on average. Depth: approximately 3 to 5 cm on average. Color (in the course of opening): Upper surface: near Red Group 36D slightly suffused with near Red Group 36C, with a large spot of near Yellow Group 2B and 2C at the base. under surface: near Yellow-White Group 158D very slightly suffused with near Red Group 36D, with a large spot of near Yellow Group 2B and 2C at the base. Color (open flower): Upper side: near white amply suffused with near Red Group 36C, 49B and 49C, with a large spot of near Yellow Group 2B and 2C at the base. Under side: near Yellow-White Group 158D very slightly margined with near Red Group 36C, with a large spot of near Yellow Group 2B and 2C at the base. Fragrance: none detected. Petal number: approximately 5 on average under normal growing conditions. Petal shape: with a substantially rounded tip and a rounded base. Petal texture: leathery and somewhat firm. Petal length: approximately 2 cm on average. Petal width: approximately 2 cm on average. Petal arrangement: imbricated, and without petaloids. Petal drop: good with the petals commonly detaching cleanly before drying. Stamen number: approximately 104 on average. Anthers: regularly arranged around the styles, approximately 1 mm in size on average, and near Yellow-Orange Group 15C in coloration. Filaments: approximately 3 mm in length on average, and near Yellow Group 2C in coloration. Pistils: approximately 33 on average. Stigmas: approximately 1 mm in size on average, and near Yellow-Green Group 150C in coloration. Styles: approximately 2 mm in length on average, and near Red Group 50C in coloration. Receptacle: smooth, pitcher-shaped in longitudinal section, approximately 7 mm in length on average, approximately 4 mm in width on average at the widest point, and near Yellow-Green Group 147C in coloration.

Development:

*Vegetation*.—Strong.

*Blooming*.—Medium season, very abundant and substantially continuous.

*Tolerance to diseases*.—Good, particularly with respect to Marsonia.

The new 'Meiajbeth' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a bushy growth habit with strong vegetation, (b) forms in abundance on a substantially continuous basis attractive near white suffused with red single blossoms, (c) exhibits dense dark green foliage with a glossy aspect on the upper surface, (d) displays good disease tolerance particularly with respect to Marsonia, and (e) is particularly well suited for providing attractive ornamentation in parks and gardens;

substantially as shown and described.

* * * * *